United States Patent [19]

Agar

[11] 4,063,448
[45] Dec. 20, 1977

[54] DENSITY METER COIL ASSEMBLY

[75] Inventor: Joram Agar, Houston, Tex.

[73] Assignee: Agar Instrumentation Inc., Houston, Tex.

[21] Appl. No.: 717,787

[22] Filed: Aug. 25, 1976

[51] Int. Cl.$^2$ .............................................. G01N 9/00
[52] U.S. Cl. ...................................... 73/32 A; 310/25
[58] Field of Search ............ 73/32 A, 32 R; 335/220, 335/229, 235, 252; 310/DIG. 1, 25

[56] References Cited

U.S. PATENT DOCUMENTS

| | | | |
|---|---|---|---|
| 1,953,542 | 4/1934 | Pridham | 310/25 |
| 2,275,839 | 3/1942 | Boehne | 335/220 |
| 2,869,050 | 1/1959 | van Urk | 335/229 |
| 2,956,431 | 10/1960 | Westerheim | 73/32 A |
| 3,600,614 | 8/1971 | Curtis | 310/25 |
| 3,763,692 | 10/1973 | Agar | 73/32 A |

FOREIGN PATENT DOCUMENTS 1,907,969   9/1969   Germany ............................ 335/229

Primary Examiner—James J. Gill
Attorney, Agent, or Firm—Beveridge, De Grandi, Kline & Lunsford

[57] ABSTRACT

An apparatus for measuring the density of a fluid including a coil assembly comprising a housing of magnetic material having first and second circular end walls and a cylindrical permanent magnet disposed between and interconnecting said first and second end walls, said second end wall having means defining a centrally disposed circular aperture therein; a pole piece which extends from the first end wall and into the said aperture; and a coil which is mounted in the housing with the said pole piece extending axially therethrough, magnetic flux passing outwardly of the housing only through said aperture and being focussed by the latter.

6 Claims, 4 Drawing Figures 4,063,448

DENSITY METER COIL ASSEMBLY

BACKGROUND OF THE INVENTION

This invention concerns a coil assembly incorporated into apparatus for measuring the density of a fluid.

In U.S. Pat. No. 3,763,692 there is disclosed an apparatus for measuring the density of a fluid in which the fluid is caused to pass through a sensing tube, the sensing tube is excited by a drive coil assembly to vibrate at a resonant frequency, and a signal, whose frequency depends upon the density of the fluid passing through the vibrating sensing tube, is produced in a detecting coil assembly.

Each of the said coil assemblies of U.S. Pat. No. 3,763,692 comprises a magnetic housing which is disposed adjacent to the sensing tube and is open on the side facing the latter, the housing containing a drive or detecting coil. The housing has a peripheral wall and a central pole piece which is coaxial with the peripheral wall and extends through said coil.

In each of the coil assemblies of U.S. Pat. No. 3,763,692 therefore, the magnetic flux between the peripheral wall and the pole piece passes outwardly of the housing through the said open side thereof and thus contacts the sensing tube over a relatively large area. In consequence, magnetic cross-coupling can occur between the two coil assemblies and this can give rise to errors in density measurement, e.g. by causing "mode jumping", i.e. by causing the mode of vibration of the sensing tube to alter.

This problem has been particularly severe in the case of such density measuring apparatus intended to be operated at high temperatures because in that case the coil has to be made of a specifically insulated wire, e.g. a ceramic insulated nickel clad copper wire, and this means that the size of the coil — and hence the size of the housing has to be greatly increased. This in turn increases the size of the said open side of the housing through which the magnetic flux passes and therefore increases the area of the sensing tube against which the said flux impinges with consequentially increased risk of magnetic cross-coupling between the two coil assemblies.

Accordingly it is an object of the invention to provide a coil assembly which, when used in an apparatus for measuring the density of a fluid, will obviate the risk of such cross-coupling.

Another object of the invention is to provide such a coil assembly suitable for use at high temperatures.

SUMMARY OF THE INVENTION

According to the present invention, there is provided a coil assembly comprising a housing of magnetic material having first and second end walls and a peripheral wall disposed between and interconnecting said first and second end walls, said second end wall having means defining a centrally disposed aperture therein; a pole piece which extends from the first end wall and into the said aperture; and a coil which is mounted in the housing with the said pole piece extending axially therethrough, magnetic flux passing outwardly of the housing only through said aperture and being focussed by the latter.

Preferably at least part of the housing is constituted by a permanent magnet.

The peripheral wall is preferably constituted by a cylindrical permanent magnet, the first and second end walls and the said aperture all being circular.

The diameter of the aperture may be not more than half the internal diameter of the peripheral wall.

Preferably, the first end wall and the pole piece form an integral core which is T-shaped in cross-section.

The coil may be made of ceramic insulated wire.

The said housing may be mounted in an externally threaded shroud which has at least one axially extending slot therein.

The second end wall is preferably constituted by a silicon iron disc.

In another aspect the present invention comprises apparatus for measuring the density of a fluid, said apparatus comprising a sensing tube adapted to have said fluid passing through its interior, a drive coil assembly for exciting said sensing tube to vibrate at a resonant frequency, and a detecting coil assembly for detecting a signal representative of the frequency of said vibrations, the frequency of said signal in operation being dependent upon the density of said fluid; each said coil assembly comprising a housing of magnetic material having first and second circular end walls and a cylindrical permanent magnet disposed between and interconnecting said first and second end walls, said second end wall having means defining a centrally disposed aperture therein; a pole piece which extends from the first end wall and into the said aperture; and a coil which is mounted in the housing with the said pole piece extending axially therethrough, magnetic flux passing outwardly of the housing only through said aperture and being focussed by the latter onto a region of said sensing tube which is remote from the region thereof onto which impinges the flux from the other coil assembly, cross-coupling between the coil assemblies being thus avoided. The said regions of the sensing tube are preferably diametrically opposite to each other.

DESCRIPTION OF THE PREFERRED EMBODIMENT

Figure 1:
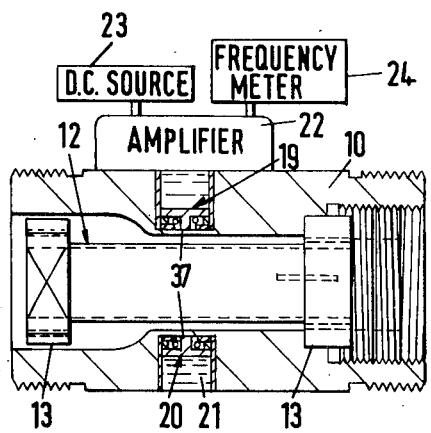
Figure 2:
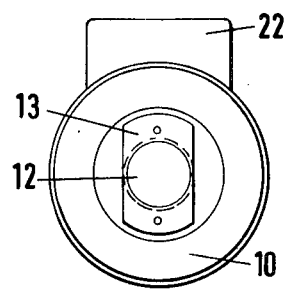
Figure 3:
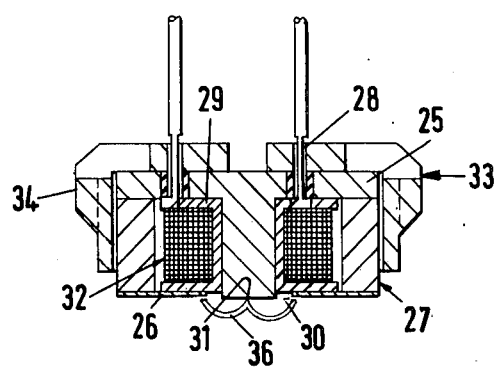
Figure 4:
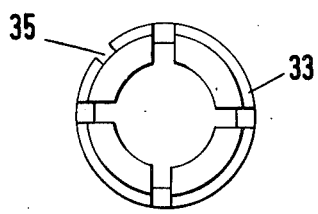

The invention is illustrated, merely by way of example, in the accompanying drawings, in which:

FIG. 1 is a sectional view of an apparatus for measuring the density of a fluid, said apparatus being provided with coil assemblies in accordance with the present invention, FIG. 2 is an end view of the apparatus shown in FIG. 1, FIG. 3 is a sectional view, on a larger scale, of a said coil assembly, and FIG. 4 is an end view of a part of the said coil assembly.

Referring first to FIGS. 1 and 2, there is shown an apparatus for measuring the density of a fluid which comprises a rigid, hollow, cylindrical casing 10. The casing 10 completely surrounds a substantially cylindrical thin-walled sensing tube 12. Each end of the sensing tube 12 is formed with a part-annular flange 13. Whereas the rigid casing 10 is made of a non-magnetic material such as aluminum or stainless steel, the sensing tube 12, is made of a magnetic material which has small thermoelastic coefficient. One such material is sold under the Trade Name ELINVAR.

It will be appreciated that when, in operation, one end of the casing 10 is exposed to fluid flow, the fluid will enter into the interior of the sensing tube 12, and owing to the part-annular shape of the flanges 13, fluid will also flow around the sensing tube 12 within the casing 10. Thus, in operation, the fluid pressures acting on the thin cylindrical wall of the sensing tube 12 will be equal.

Mounted at approximately the mid-portion of the casing 10 are a drive coil assembly 19 and a detecting coil assembly 20 located to be adjacent the area of maximum vibration amplitude of the sensing tube 12. The coil assemblies 19, 20 are arranged and maintained in operation at a 90° phase difference between the driving force of the coil assembly 19 and the detected velocity of the change in the spacing of the sensing tube 12 and the detecting coil assembly 20, which results in an arrangement in which viscosity effects are substantially reduced or eliminated.

The coil assemblies 19 and 20 are secured in place on the casing 10 by means of a filler element 21.

Mounted on the exterior of the casing 10 is an amplifier 22 to which are electrically connected both the drive coil assembly 19 and the detecting coil assembly 20. The amplifier 22 itself is connected to a small d.c. power source 23, e.g. a 12 volt battery, and the output circuit of the amplifier is connected to a frequency meter 24 or a periodic time meter.

As shown in FIG. 3, each of the coil assemblies 19, 20 comprises a housing of magnetic material, the housing comprising end walls 25, 26 which are circular in plan. Disposed between and interconnecting the end walls 25, 26 is a peripheral wall constituted by a cylindrical permanent magnet 27. The end wall 26, which is constituted by an annular disc of silicon iron, has a centrally disposed circular aperture 30 therein, the diameter of the aperture 30 being not more than half the internal diameter of the cylindrical permanent magnet 27.

The end wall 25, together with a pole piece 31 which extends therefrom, form an integral core which is T-shaped in cross-section, the pole piece 31 extending axially through the aperture 30. The core may be made of PERMENDUR, or other material having low hysteresis properties.

Mounted in the said housing, on a bobbin 29 of non-magnetic material, is a coil 32 e.g. of ceramic insulated, nickel-clad copper, wire 28, the pole piece 31 extending axially through the coil 32.

The housing is mounted within a shroud 33 which is externally threaded at 34 for retention in a correspondingly threaded recess in the casing 10. The shroud 33 may be provided with one or more axially extending air release slots 35 (FIG. 4). The parts of the coil assembly may be bonded together with a ceramic paste, and the slot or slots 35 provide for the release of air during firing and curing.

As shown in FIG. 3, the lines 36 of magnetic flux between the disc 26 and the pole piece 31 pass outwardly of the housing only through the aperture 30 and are focussed by the latter so that they pass through an adjacent part 37 of the casing 10 and onto a small region of the sensing tube 12, being substantially tangential to the latter. Thus the cylindrical permanent magnet 27 and the circular aperture 30 in the disc 26 respectively act in a manner comparable to a cylindrical light source and a converging lens to produce a focussed "beam" of flux.

Although the bobbin 29 physically occludes the aperture 30 it has no effect on the magnetic focussing achieved by the coil assembly since the flux passes through the wall of the bobbin 29 adjacent the aperture 30.

The operation of the apparatus is as follows:

The rigid casing 10 with the sensing tube 12 securely mounted therein is exposed to fluid flow passing therethrough. With the power source 23 connected to the amplifier 22, natural resonant vibrations will be set up and maintained in the sensing tube 12 by virtue of the positive feed-back from the detecting coil assembly 20 to the drive coil assembly 19. The vibrations are initiated by mechanical noise transmitted to the sensing tube 12 or by electrical noise occurring in the drive coil assembly 19 when the amplifier 22 is switched into action. The end flanges 13 of the sensing tube 12 allow it to be clamped without affecting the frequency of its oscillation and without interfering with the flow of fluid therethrough.

The drive coil assembly 19 focusses the magnetic flux 36 therefrom onto a region of the sensing tube 12 which is diametrically opposite to, and hence remote from, the region of the sensing tube 12 onto which is focussed the magnetic flux from the detecting coil assembly 20. Cross-coupling between the coil assemblies 19, 20 is thus avoided.

As will be appreciated in the case of the present invention the actual size of the housings of the coil assemblies is not of great importance since the flux is emitted therefrom only through the respective aperture 30. Consequently, the housings can readily be made large enough to accommodate a coil 32 made of a heavily insulated and thus thick wire intended for use at high temperatures.

What I claim is:

1. Apparatus for measuring the density of a fluid, said apparatus comprising a sensing tube adapted to have said fluid passing through its interior, a drive coil assembly for exciting said sensing tube to vibrate at a resonant frequency, and a detecting coil assembly for detecting a signal representative of the frequency of said vibrations, the frequency of said signal in operation being dependent upon the density of said fluid; each said coil assembly comprising a housing of magnetic material having first and second circular end walls and a cylindrical permanent magnet disposed between and interconnecting said first and second end walls, said second end wall having means defining a centrally disposed aperture therein; a pole piece which extends from the first end wall and into the said aperture; and a coil which is mounted in the housing with the said pole piece extending axially therethrough, magnetic flux passing outwardly of the housing only through said aperture and being focussed by the latter onto a region of said sensing tube which is diametrically opposite to the region thereof onto which impinges the flux from the other coil assembly, cross-coupling between the coil assemblies being thus avoided.

2. Apparatus as claimed in claim 1 in which the aperture of each coil assembly is circular and has a diameter which is not more than half the internal diameter of the peripheral wall thereof.

3. Apparatus as claimed in claim 1 in which the first end wall and the pole piece of each coil assembly form an integral core which is T-shaped in cross-section.

4. Apparatus as claimed in claim 1 in which the coil of each coil assembly is made of ceramic insulated wire.

5. Apparatus as claimed in claim 1 in which the said housing of each coil assembly is mounted in an externally threaded shroud which has at least one axially extending slot therein.

6. Apparatus as claimed in claim 1 in which the second end wall of each coil assembly is constituted by a silicon iron disc.

* * * * *